United States Patent [19]
Chang

[11] Patent Number: 5,880,139
[45] Date of Patent: Mar. 9, 1999

[54] TRIARYL SUBSTITUTED IMIDAZOLES AS GLUCAGON ANTAGONISTS

[75] Inventor: Linda L. Chang, Wayne, N.J.

[73] Assignee: Merck & Co., Inc., Rahway, N.J.

[21] Appl. No.: 972,023

[22] Filed: Nov. 17, 1997

Related U.S. Application Data

[60] Provisional application No. 60/031,466 Nov. 20, 1996.

[51] Int. Cl.⁶ .......................... A61K 31/44; C07D 401/04
[52] U.S. Cl. ......................................... 514/326; 546/274.1
[58] Field of Search .......................... 546/274.1; 514/326

[56] References Cited

U.S. PATENT DOCUMENTS 3,772,441  11/1973  Lombardino .
3,929,807  12/1975  Fitzi .
5,620,999   4/1997  Weier et al. .
5,686,455  11/1997  Adams et al. .

FOREIGN PATENT DOCUMENTS

WO 93/14081  7/1993  WIPO .
WO 95/03297  2/1995  WIPO .
WO 96/03387  2/1996  WIPO .
WO96/18626   6/1996  WIPO .

*Primary Examiner*—Robert W. Ramsuer
*Attorney, Agent, or Firm*—Mollie M. Yang; David L. Rose

[57] ABSTRACT

2,4-Diaryl-5-pyridylimidazoles are glucagon antagonists. The compounds block the action of glucagon at its receptor. Thus, the compounds can be used in the prophylaxis or treatment of disease states in mammals mediated by elevated levels of glucagon. Examples of such disease states include diabetes, obesity, hypertension, and cachexia and the like.

3 Claims, No Drawings

TRIARYL SUBSTITUTED IMIDAZOLES AS GLUCAGON ANTAGONISTS

CROSS REFERENCE TO RELATED APPLICATIONS

This application is based on, and claims priority from, provisional application 60/031,466 filed on Nov. 20, 1996.

BACKGROUND OF THE INVENTION

The present invention relates to triaryl substituted imidazoles which antagonize the metabolic effect of glucagon. This invention also relates to compositions containing such compounds and methods of treatment using such compounds.

Diabetes is a disease process derived from multiple causative factors and characterized by elevated levels of plasma glucose. Uncontrolled hyperglycemia is associated with an increased risk for microvascular and macrovascular diseases, including nephropathy, retinopathy, hypertension, stroke and heart disease. Control of glucose homeostasis is, therefore, a major approach to the treatment of diabetes.

Glucagon is a major counter regulatory hormone that attenuates the inhibition of liver gluconeogenesis by insulin. Glucagon receptors are found primarily in the liver, although their presence has been documented in kidney, pancreas, adipose tissues, heart, smooth muscles of vascular tissues, and some regions of the brain, stomach and adrenal glands.

Type II diabetics have elevated levels of plasma glucagon and increased rates of hepatic glucose production. The rate of hepatic glucose production positively correlates with fasting blood glucose levels in type II diabetics. Therefore, antagonists of glucagon are useful in improving insulin responsiveness in the liver, decreasing the rate of gluconeogenesis and lowering the rate of hepatic glucose output resulting in a decrease in the levels of plasma glucose.

A monoclonal antibody to glucagon (Glu-mAb) has been utilized to test the acute effects of attenuation of glucagon action in streptozotocin-treated diabetic rats (Brand et al., Diabetologia 37:985, 1994). In contrast to a control antibody, injection of Glu-mAb attenuated the postprandial increase in blood glucose in moderately hyperglycemic rats (ie., rats with a moderate impairment in insulin secretion). In severely hyperglycemic rats (ie., rats with severely impaired insulin secretion), Glu-mAb injection did not lower blood glucose levels, but potentiated the hypoglycemic effect of a suboptimal dose of insulin. These data suggest that attenuation of the action of glucagon in these models leads to increased sensitivity to the action of insulin, but does not lead to decreased blood glucose levels in the absence of insulin. On the other hand, a monoclonal antibody to glucagon was effective in lowering plasma glucose levels in diabetic rabbits independent of insulin effects (Brand et al., Diabetes, 45:1076 (1996). While these data support the notion that antagonism of glucagon action will provide beneficial therapy for both type I and type II diabetics, this hypothesis could be more rigorously tested if a specific non-peptidyl glucagon antagonist were available.

The regulation of glucagon homeostasis is also mediated by the hormone insulin, produced in the β cells of the pancreas. Deterioration of these cells is typically observed in Type I diabetics, and abnormalities in the function of these cells may occur in patients presenting the symptoms of Type II diabetes. Thus, a glucagon antagonist might have utility in treating Type I diabetics.

The glucagon receptor is expressed in kidney tissues where glucagon has been demonstrated to have an effect on electrolyte homeostasis including the ions sodium, potassium, chloride, magnesium, calcium, and phosphate and the non-electrolytes urea and water (Ahloulay et al., Am. J. Physiol., 269: F225, 1995). A glucagon antagonist may have use in treating disorders involving electrolyte imbalance. The kidney is also gluconeogenic in response to glucagon (Amores et al., Molec. Cell. Biochem., 137: 117, 1994) and an antagonist would act to lower glucose production in kidney furthering the treatment of diabetes.

Glucagon receptors are present in the heart and in smooth muscles. Glucagon has a direct effect on cardiac output and heart rate (Glick et al., Circ. Res., 22: 789 (1968); Farah, Pharm. Rev., 35: 181, 1983). A strong correlation has been observed in patients with hypertension and elevated plasma glucagon levels resulting from impaired hepatic catabolism (Silva et al., Heptatology, 11: 668, 1990). Antagonism of the effects of elevated glucagon levels may have an effect on certain types of hypertension, thus a glucagon antagonist may have utility in the treatment of certain types of hypertension associated with elevated glucagon production.

The primary role for glucagon and glucagon receptors associated with adipose tissues is to induce lipolysis, thus providing free fatty acids as a substrate for fat burning tissues (Saggerson et al., Biochem. J., 238: 387, 1986). An antagonist to this effect might be useful in treating conditions where there is excessive lipolysis of fat stores resulting from elevated glucagon levels, such as wasting disease (cachexia).

Glucagon and glucagon receptors have been localized to the hippocampus region of the brain (Hoosein and Gurd, Proc. Natl. Acad. Sci. USA, 81: 4368, 1984). This discovery suggests that glucagon may have a neuroendocrine role in initiating or elaborating basic behavior or somatic motor programs. Since glucagon secretion is increased in response to low blood glucose levels, increased glucagon levels in the brain may initiate behavior to respond to low glucose levels, such as eating. Thus, chronic hyperglucagonemia may also result in a constant craving for food resulting in obesity. A glucagon antagonist may have utility in treating obesity by altering feeding behavior associated with a response to glucagon.

The compounds in the present invention are glucagon antagonists. The compounds block the action of glucagon at its receptors and thereby decrease the levels of plasma glucose. The instant compounds thus are useful as antidiabetic agents. Glucagon may have other direct effects on cardiac output, lipolysis, and feeding behavior and therefore may be useful as antihypertensive, anti-cachexia or antiobesity agents.

SUMMARY OF THE INVENTION

The present invention relates to 2,4-diaryl-5-pyridyl imidazoles which are glucagon receptor antagonists. These compounds are therefore useful for the treatment of diseases caused by excessive levels of glucagon, including diabetes and certain types of hypertension, cachexia and obesity.

Also included in the invention are pharmaceutical compositions which comprise a compound of formula I in combination with a pharmaceutically acceptable carrier.

Also included in the invention are methods of treating glucagon-mediated disease, comprising administering to a mammalian patient in need of such treatment an amount of a compound of formula I which is effective to treat said disease.

DETAILED DESCRIPTION OF THE INVENTION

The present invention provides compounds of formula (1):

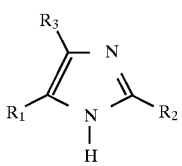

(I)

wherein $R_1$ is 4-pyridyl, 4-pyrimidinyl or 4-quinolyl which is unsubstituted or substituted with one or two substituents each of which is independently selected from the group consisting of
  (1) halogen,
  (2) —CN,
  (3) $C_{1-10}$ alkyl, wherein said alkyl is optionally substituted with from 1 to 5 halogen atoms,
  (4) —O—$C_1$_alkyl,
  (5) —S—$C_{1-10}$ alkyl,
  (6) —$NR_8R_9$, and
  (7) —$NO_2$;

$R_2$ is phenyl, 1-naphthyl, 2-naphthyl or heteroaryl which is unsubstituted or substituted with one, two or three substituents each of which is independently selected from the group consisting of
  (1) $C_{1-10}$ alkyl,
  (2) $R_4$, and
  (3) $C_{1-10}$ alkyl substituted with up to 5 groups independently selected from $R_4$;

$R_3$ is phenyl, which is unsubstituted or substituted with one or two substituents each of which is independently selected from the group consisting of
  (1) $C_{4-10}$ alkyl, wherein said alkyl is optionally substituted with from 1 to 5 halogen atoms,
  (2) —O—$C_{3-10}$ alkyl,
  (3) —O—$C_{1-4}$ alkylaryl,
  (4) —S—$C_{2-10}$ alkyl,
  (5) —$S(O)_mC_{3-10}$ alkyl,
  (6) —$C(O)C_{3-10}$ alkyl,
  (7) —$CO_2C_{3-10}$ alkyl,
  (8) —$NR_7R_{17}$,
  (9) meta-O-phenyl, which is optionally substituted with halo, $C_{1-4}$ alkyl, or $C_{1-4}$ alkoxy;

$R_4$ is
  (1) —$OR_8$,
  (2) —$NO_2$,
  (3) halogen
  (4) —$S(O)_mR_{11}$,
  (5) —$SR_8$,
  (6) —$S(O)_mOR_8$,
  (7) —$S(O)_mNR_8R_9$,
  (8) —$NR_8R_9$,
  (9) —$O(CR_{10}R_{30})_pNR_8R_9$,
  (10) —$C(O)R_8$,
  (11) —$CO_2R_8$,
  (12) —$CO_2(CR_{10}R_{20})_nCONR_8R_9$,
  (13) —$ZC(O)R_8$,
  (14) —CN,
  (15) —$C(Z)NR_8R_9$,
  (16) $NR_{10}C(Z)R_8$,
  (17) —$C(Z)NR_8OR_9$,
  (18) $NR_{10}C(Z)NR_8R_9$,
  (19) —$NR_{10}S(O)_mR_{11}$,
  (20) —$C(=NOR_{21})R_8$,
  (21) —$NR_{10}C(=NR_{15})SR_{11}$,
  (22) —$NR_{10}C(=NR_{15})NR_8R_9$,
  (23) —$NR_{10}C(=CR_{14}R_{24})SR_{11}$,
  (24) —$NR_{10}C(=CR_{14}R_{24})NR_8R_9$,
  (25) —$NR_{10}C(O)C(O)NR_8R_9$,
  (26) —$NR_{10}C(O)C(O)OR_{10}$,
  (27) —$C(=NR_{13})NR_8R_9$,
  (28) —$C(=NOR_{13})NR_8R_9$,
  (29) —$C(=NR_{13})ZR_{11}$,
  (30) —$OC(Z)NR_8R_9$,
  (31) —$NR_{10}S(O)_mCF_3$,
  (32) —$NR_{10}C(Z)OR_{10}$,
  (33) 5-($R_{18}$)-1,2,4-oxadiazol-3-yl or
  (34) 4-($R_{12}$)-5-($R_{18}R_{19}$)-4,5-dihydro-1,2,4-oxadiazol-3-yl;

$R_7$ and $R_{17}$ are each independently selected from hydrogen or $C_{1-4}$ alkyl provided that $R_7$ and $R_{17}$ are not both hydrogen; or $R_7$ and $R_{17}$ together with the nitrogen to which they are attached form a heterocyclic ring of 5 to 7 members which ring optionally contains an additional heteroatom selected from oxygen, sulfur or $NR_{22}$;

$R_8$ and $R_9$ are independently selected from
  (1) hydrogen,
  (2) heterocyclyl,
  (3) heterocyclyl-$C_{1-10}$ alkyl, and
  (4) $R_{11}$; or $R_8$ and $R_9$ together with the nitrogen to which they are attached form a heterocyclic ring of 5 to 7 members which ring optionally contains an additional heteroatom selected from oxygen, sulfur or $NR_{12}$;

$R_{10}$ and $R_{20}$ is each independently selected from hydrogen or $C_{1-4}$ alkyl;

$R_{11}$ is
  (1) $C_{1-10}$ alkyl,
  (2) halo-substituted $C_{1-10}$ alkyl,
  (3) $C_{2-10}$ alkenyl,
  (4) $C_{2-10}$ alkynyl,
  (5) $C_{3-7}$ cycloalkyl,
  (6) $C_{5-7}$ cycloalkenyl,
  (7) aryl,
  (8) aryl-$C_{1-10}$ alkyl,
  (9) heteroaryl or
  (10) heteroaryl-$C_{1-10}$ alkyl;

$R_{12}$ is
  (1) hydrogen,
  (2) —$C(Z)R_{13}$,
  (3) optionally substituted $C_{1-10}$ alkyl, wherein the substituents may be halo, $C_{1-3}$ alkoxy, amino, or carboxy,
  (4) optionally substituted aryl $C_{1-10}$ alkyl, wherein the substituents may be halo, $C_{1-3}$ alkoxy, amino, or carboxy, or
  (5) $S(O)_2R_{25}$;

$R_{13}$ is
  (1) hydrogen, or
  (2) $R_{25}$;

$R_{14}$ and $R_{24}$ is each independently selected from
  (1) hydrogen,
  (2) $C_{1-4}$ alkyl,
  (3) nitro or
  (4) cyano;

$R_{15}$ is
  (1) hydrogen,
  (2) cyano,
  (3) $C_{1-4}$ alkyl,
  (4) $C_{3-7}$ cycloalkyl or
  (5) aryl;

$R_{18}$ and $R_{19}$ is each independently selected from
  (1) hydrogen, (2) $C_{1-4}$ alkyl,
(3) substituted $C_{1-4}$ alkyl, wherein the substituents may be halo, $C_{1-3}$ alkoxy, amino, or carboxy,
(4) optionally substituted aryl, wherein the substituents may be halo, $C_{1-3}$ alkoxy, amino, or carboxy,
(5) optionally substituted aryl-$C_{1-10}$ alkyl, wherein the substituents may be halo, $C_{1-3}$ alkoxy, amino, or carboxy, or $R_{18}$ and $R_{19}$ together denote an oxo or thioxo;

$R_{21}$ is
(1) $R_{13}$,
(2) a pharmaceutically acceptable cation, or
(3) aroyl, or
(4) $C_{1-10}$ alkanoyl;

$R_{22}$ is
$R_{10}$ or $C(Z)$—$C_{1-4}$ alkyl;

$R_{25}$ is (1) $C_{1-10}$ alkyl,
(2) $C_{3-7}$ cycloalkyl,
(3) heterocyclyl,
(4) aryl,
(5) aryl $C_{1-10}$ alkyl,
(6) heterocyclyl-$C_{1-10}$ alkyl,
(7) heteroaryl or
(8) heteroaryl $C_{1-10}$ alkyl;

Z is oxygen or sulfur;
m is 1 or 2;
n is 1 to 10;
p is 1 to 10; or
a pharmaceutically acceptable salt thereof.

In one subset of the present compounds, there are provided compounds of formula (I) wherein $R_1$ is 4-pyridyl which is unsubstituted or substituted with one or two substituents each of which is independently selected from the group consisting of
(1) halogen,
(2) —CN,
(3) $C_{1-10}$ alkyl, wherein said alkyl is optionally substituted with from 1 to 5 halogen atoms,
(4) —O—$C_{1-10}$ alkyl,
(5) —S—$C_{1-10}$ alkyl,
(6) —$NR_8R_9$, and
(7) —$NO_2$.

In a further subset of the present compounds, there are provided compounds of formula (I) wherein $R_2$ is phenyl, 1-naphthyl or 2-naphthyl each of which is unsubstituted or substituted with one, two or three groups each of which is independently selected from the group consisting of
(1) $C_{1-10}$ alkyl,
(2) $R_4$, and
(3) $C_{1-10}$ alkyl substituted with up to 5 groups independently selected from $R_4$.

Another subset of the present compounds provides compounds of formula (I) wherein $R_3$ is phenyl, which is unsubstituted or substituted with one or two substituents each of which is independently selected from the group consisting of
(1) $C_{4-10}$ alkyl, wherein said alkyl is optionally substituted with from 1 to 5 halogen atoms,
(2) —O—$C_{3-10}$ alkyl,
(3) —O—$C_{1-4}$ alkylaryl,
(4) —S—$C_{2-10}$ alkyl,
(5) meta-O-phenyl, which is optionally substituted with halo, $C_{1-4}$ alkyl, or $C_{1-4}$ alkoxy;

In a preferred embodiment there are provided compounds of formula (I) wherein $R_1$ is 4-pyridyl or 4-quinolyl;

$R_2$ is phenyl which is unsubstituted or substituted with one, two or three substituents each of which is independently selected from the group consisting of
(1) $C_{1-10}$ alkyl,
(2) $R_4$, and
(3) $C_{1-10}$ alkyl substituted with up to 5 groups independently selected from $R_4$;

$R_3$ is phenyl substituted with one or two substituents each of which is independently selected from the group consisting of
(1) $C_{4-10}$ alkyl, wherein said alkyl is optionally substituted with from 1 to 5 halogen atoms,
(2) —O—$C_{3-10}$ alkyl,
(3) —O—$C_{1-2}$ alkylaryl,
(4) —S—$C_{2-10}$ alkyl,
(5) meta-O-phenyl, which is optionally substituted with halo, $C_{1-4}$ alkyl, or $C_{1-4}$ alkoxy;

$R_4$ is
(1) —$OR_8$,
(2) halogen $R_8$ is selected from
(1) hydrogen, and
(2) $R_{11}$; and $R_{11}$ is
(1) $C_{1-10}$ alkyl,
(2) halo-substituted $C_{1-10}$ alkyl,
(3) $C_{3-7}$ cycloalkyl,
(4) aryl,
(5) aryl-$C_{1-10}$ alkyl, or
a pharmaceutically acceptable salt thereof.

In a further preferred embodiment there are provided compounds of formula (I) wherein $R_1$ is 4-pyridyl;

$R_2$ is phenyl which is substituted with one or two substituents each of which is independently selected from the group consisting of
(1) $C_{1-10}$ alkyl,
(2) $R_4$, and
(3) $C_{1-10}$ alkyl substituted with up to 5 groups independently selected from halogen $R_3$ is phenyl substituted with one or two substituents each of which is independently selected from the group consisting of
(1) $C_{4-10}$ alkyl, wherein said alkyl is optionally substituted with from 1 to 5 halogen atoms,
(2) —O—$C_{3-10}$ alkyl,
(3) —O—$C_{1-2}$ alkylaryl,
(4) —S—$C_{2-10}$ alkyl,
(5) meta-O-phenyl, which is optionally substituted with halo, $C_{1-4}$ alkyl, or $C_{1-4}$ alkoxy;

$R_4$ is
(1) —$OR_8$,
(2) halogen;

$R_8$ is $R_{11}$;

$R_{11}$ is
(1) $C_{1-10}$ alkyl,
(2) halo-substituted $C_{1-10}$ alkyl,
(3) $C_{3-7}$ cycloalkyl,
(4) aryl,
(5) aryl-$C_{1-10}$ alkyl, or
a pharmaceutically acceptable salt thereof.

Especially preferred compounds of formula I include:
(1) 2-(4-chlorophenyl)-4-(3-phenoxyphenyl)-5-(4-pyridyl) imidazole (2) 2-(3-chlorophenyl)-4-(3-phenoxyphenyl)-5-(4-pyridyl)imidazole
(3) 2-(3,4-dichlorophenyl)-4-(3-phenoxyphenyl)-5-(4-pyridyl)imidazole
(4) 2-(4-phenoxyphenyl)-4-(3-phenoxyphenyl)-5-(4-pyridyl)imidazole
(5) 4-(4-n-butylphenyl)-2-(4-chlorophenyl)-5-(4-pyridyl)imidazole
(6) 4-(4-n-butylphenyl)-2-(3-chlorophenyl)-5-(4-pyridyl)imidazole
(7) 4-(4-t-butylphenyl)-2-(4-chlorophenyl)-5-(4-pyridyl)imidazole
(8) 4-(4-t-butylphenyl)-2-(3-chlorophenyl)-5-(4-pyridyl)imidazole
(9) 2-(4-chlorophenyl)-4-(4-n-propyloxyphenyl)-5-(4-pyridyl)imidazole
(10) 2-(4-chlorophenyl)-4-(4-ethylthiophenyl)-5-(4-pyridyl)imidazole
(11) 4-(3-phenoxyphenyl)-5-(4-pyridyl)-2-(4-trifluoromethylphenyl)-imidazole
(12) 2-(4-bromophenyl)-4-(3-phenoxyphenyl)-5-(4-pyridyl)imidazole
(13) 2-(4-fluorophenyl)-4-(3-phenoxyphenyl)-5-(4-pyridyl)imidazole
(14) 2-(4-benzyloxyphenyl)-4-(3-phenoxyphenyl)-5-(4-pyridyl)imidazole
(15) 2-(3-fluorophenyl)-4-(3-phenoxyphenyl)-5-(4-pyridyl)imidazole
(16) 4-(3-n-butyloxyphenyl)-2-(4-chlorophenyl)-5-(4-pyridyl)imidazole
(17) 4-(2-n-butyloxyphenyl)-2-(4-chlorophenyl)-5-(4-pyridyl)imidazole
(18) 2-(4-chlorophenyl)-4-(2,4-di(n-propyloxy)phenyl)-5-(4-pyridyl)imidazole
(19) 2-(4-chlorophenyl)-4-(2,4-di(n-butyloxy)phenyl)-5-(4-pyridyl)imidazole
(20) 4-(4-benzyloxyphenyl)-2-(4-chlorophenyl)-5-(4-pyridyl)imidazole.

For the purposes herein of nomenclature, the compounds of formula I are named by their position corresponding to:

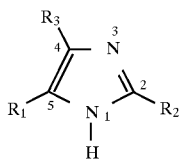

The invention is described herein in detail using the terms defined below unless otherwise specified.

"Halogen" includes fluorine, chlorine, bromine and iodine.

The term "alkyl" refers to a monovalent alkane (hydrocarbon)-derived radical containing the designated number of carbon atoms. It may be straight or branched. Examples include methyl, ethyl, propyl, butyl, pentyl, hexyl, isopropyl, sec-butyl, isopentyl and t-butyl.

The term "alkenyl" refers to a hydrocarbon radical, straight or branched, containing the designated number of carbon atoms and at least one carbon to carbon double bond. Preferably one carbon to carbon double bond is present, and up to four non-aromatic (non-resonating) carbon-carbon double bonds may be present. Examples of alkenyl groups include ethenyl, propenyl, butenyl and isobutenyl.

The term "alkynyl" refers to a hydrocarbon radical, straight or branched, containing the designated number of carbon atoms and at least one carbon to carbon triple bond. Up to three carbon-carbon triple bonds may be present. Examples of alkynyl groups include ethynyl, propynyl and butynyl.

Aryl refers to aromatic rings including phenyl and naphthyl.

The term "heteroaryl" (on its own or in any combination, such as "heteroaryloxy") represents a 5–10 membered aromatic ring system in which one or more rings contain one or more heteroatoms selected from the group consisting of N, O and S, such as, but not limited to pyridyl, pyrimidinyl, pyrrolyl, furyl, thienyl, imidazolyl, thiazolyl, thiadiazolyl, tetrazolyl, triazolyl, oxadiazolyl, oxazolyl, imidazolidinyl, pyrazolyl, isoxazolyl, benzothiadiazolyl, indolyl, indolinyl, benzodioxolyl, benzodioxanyl, benzothiophenyl, benzofuranyl, benzimidazolyl, benzoxazinyl, benzisoxazolyl, benzothiazolyl, 2,3-dihydrobenzofuranyl, quinolinyl, isoquinolinyl, benzotriazolyl, benzoxazolyl, 1,2,3,4-tetrahydroisoquinolinyl, 1,2,3,4-tetrahydroquinolinyl, purinyl, furopyridine and thienopyridine, tetrahydrobenzothiazolyl, 5,6,7,8-tetrahydroquinolinyl, 2,3-cyclopentenopyridyl, 4,5,6,7-tetrahydroindolyl, 5,6,7,8-tetrahydroisoquinolyl, and 5,6,7,8-tetrahydroquinoxalinyl.

"Heterocyclic" (on its own or in any combination, such as "heterocyclylalkyl") represents a saturated or partially unsaturated 4–10 membered ring system in which one or more rings contain one or more heteroatoms selected from the group consisting of N, O and S. Examples of heterocyclyls are piperidinyl, morpholinyl, pyrrolidinyl, tetrahydrofuranyl, tetrahydroimidazo[4,5-c]pyridine, imidazolinyl, piperazinyl, pyrazolindinyl and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The compounds of the present invention may contain one or more asymmetric carbon atoms and may occur as racemates, racemic mixtures, and as individual diastereomers, with all possible isomers, including optical isomers, being included within the scope of the present invention.

Throughout the instant application, the following abbreviations are used with the following meanings:

Bu butyl
Bn benzyl
BOC, Boc t-butyloxycarbonyl
BOP Benzotriazol-1-yloxy tris/dimethylamino)-phosphonium hexafluorophosphate
CBZ, Cbz Benzyloxycarbonyl
DCC Dicyclohexylcarbodiimide
DCM dichloromethane
DIEA diisopropylethylamine
DMF N,N-dimethylformamide
DMAP 4-Dimethylaminopyridine
DSC N,N'-disuccinimidyl carbonate
DTT dithiothreitol
EDC 1-(3-dimethylaminopropyl)-3-ethylcarbodiimide hydrochloride
Et ethyl
EtOAc ethyl acetate
EtOH ethanol eq. equivalent(s)
FAB-MS Fast atom bombardment-mass spectroscopy
HOAc acetic acid
HPLC High pressure liquid chromatography
HOBT, HOBt Hydroxybenztriazole
H human serum
KHMDS Potassium bis(trimethylsilyl)amide
LAH Lithium aluminum hydride
LHMDS Lithium bis(trimethylsilyl)amide
Me methyl
MHz Megahertz
MPLC Medium pressure liquid chromatography
NMM N-Methylmorpholine
NMR Nuclear Magnetic Resonance
PBS phosphate buffer saline
Ph phenyl
TFA Trifluoroacetic acid
THF Tetrahydrofuran
TLC Thin layer chromatography
TMS Tetramethylsilane The term "pharmaceutically acceptable salts" refers to salts prepared from pharmaceutically acceptable non-toxic acids or bases including inorganic acids/bases and organic acids/bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabanine, isopropylamine, lysine, methylglucamine, morpholine, piperazine, piperidine, polyamine resins, procaine, purines, theobromine, triethylamine, trimethylamine, tripropylamine, tromethamine, and the like.

Salts derived from inorganic acids include hydrochloric, hydrobromic, sulfuric, sulfamic, phosphoric, nitric and the like; and the salts prepared from organic acids include acetic, propionic, succinic, glycolic, stearic, lactic, malic, tartaric, citric, ascorbic, pamoic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

This invention relates to a method of inhibiting the action of glucagon at its receptors thereby reducing the rate of gluconeogenesis and the concentration of glucose in plasma. Thus, compounds of formula I can be used in the prophylaxis or treatment of disease states in mammals mediated by elevated levels of glucagon. Examples of such disease states include diabetes, obesity, hypertension, and cachexia and the like.

The compounds of formula I are normally formulated in accordance with standard pharmaceutical practice as a pharmaceutical composition. This invention, therefore, also relates to a pharmaceutical composition comprising a compound of formula I and a pharmaceutically acceptable carrier or diluent. The pharmaceutical carrier employed may be, for example, solid or liquid. Solid carriers include lactose, terra alba, sucrose, talc, gelatin, agar, pectin, acacia, magnesium stearate, stearic acid and the like. Liquid carriers include syrup, peanut oil, olive oil, water and the like. Similarly, the carrier may include time delay material, such as glyceryl monostearate or glyceryl distearate, alone or with a wax.

The compounds of formula I are administered in conventional dosage forms prepared by combining a compound of formula I with standard pharmaceutical carriers according to conventional procedures. The compounds of formula I may also be administered in conventional dosages in combination with a known, second therapeutically active compound. These procedures may involve mixing, granulating and compressing or dissolving the ingredients as appropriate to the desired preparation.

The active compounds of the present invention may be orally administered as a pharmaceutical composition, for example, with an inert diluent, or with an assimilable edible carrier, or they may be enclosed in hard or soft shell capsules, or they may be compressed into tablets, or they may be incorporated directly with the food of the diet. For oral therapeutic administration, which includes sublingual administration, these active compounds may be incorporated with excipients and used in the form of tablets, pills, capsules, ampules, sachets, elixirs, suspensions, syrups, and the like. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally, for example intravenously, intramuscularly, intradermally or subcutaneously. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of formula I may also be administered topically in the form of a liquid, solid or semi-solid. Liquids include solutions, suspensions and emulsions. Solids include powders, poultices and the like. Semi-solids include creams, ointments, gels and the like.

Drops according to the present invention may comprise sterile aqueous or oil solutions or suspensions, and may be prepared by dissolving the active ingredient in a suitable aqueous solution, optionally including a bactericidal and/or fungicidal agent and/or any other suitable preservatives and optionally including a surface active agent.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as steric or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

Compounds of the present invention may also be administered intranasally as, for example, liquid drops or spray; by intranasal or oral inhalation; rectally; trasdermally; or vaginally.

The amount of a compound of formula I, for the methods of use disclosed herein, vary with the compound chosen, the mode of administration, the nature and severity of the condition being treated, and other factors left to the discretion of the physician. A representative dosing regimen for treating diabetes mellitus and/or hyperglycemia may involve administering a compound of formula I at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

Compounds similar to Formula I have been described previously as cytokine inhibitors (WO93114081; WO95/03297), antiinflammatory agents (WO96/03387), and protein kinase inhibitors (WO96118626). None of these publications describe or claim treatment of diabetes by antagonism of the glucagon receptor by compounds of Formula I.

Compounds of the present invention may be prepared by several general synthetic methods as described in, for example, M. R. Grimmett, *Comprehensive Heterocyclic Chemistry, The Structure, Reactions, Synthesis and Uses of Heterocyclic Compounds,* A. R. Katritzky and C. W. Rees, eds., Vol. 5, Pergamon Press, Oxford, 1984, pp. 457–498. The compounds of the present invention can be prepared by procedures illustrated in the accompanying schemes. The three general methods for preparation of the imidazole nucleus are outlined in Schemes 1 and 2.

In the first method (Scheme 1), a suitably protected alcohol (1) (e.g., when $R_1$ is 4-pyridyl, (1) is 4-(t-butyldimethylsilyloxymethylpyridine), is deprotonated with a strong base such as lithium diisopropyl amide or n-butyl lithium and the resulting anion is reacted with an appropriate N,O-dimethylhydroxamide (2) to give a protected α-hydroxy ketone (α). The protected αhydroxy ketone is then condensed with a suitably functionalized aldehyde (4) in the presence of copper(II) acetate and ammonium acetate in acetic acid to form the desired compound (5).

Scheme 1.

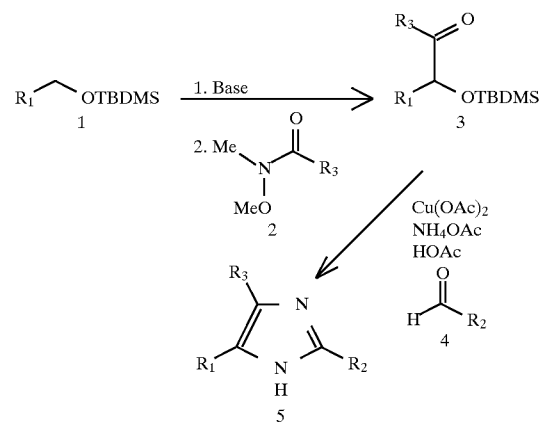

In the second method (Scheme 2), an heteroarylmethane (6) (e.g., when $R_1$ is 4-pyridyl, (6) is 4-picoline) is deprotonated with a strong base such as lithium diisopropyl amide or n-butyl lithium and the resulting anion is reacted with N,O-dimethylhydroxamide (2) to give a ketone (7). The dione (8) is obtained by selenium dioxide oxidation of the ketone (7) and then condensed with a suitably functionalized aldehyde (4) in the presence of ammonium acetate in acetic acid to form the desired imidazole (5).

Scheme 2.

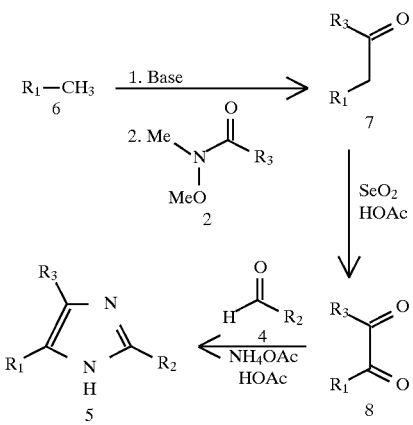

In the various synthetic methods described above, protection and deprotection of functional groups such as hydroxyl and amino groups may be required. The selection of the appropriate protecting groups, and methods for introducing and removing the protecting groups are within the knowledge of one skilled in the art, and are also described in standard reference books such as Greene and Wuts, *Protective Groups in Organic Synthesis*, 2d Ed., John Wiley & Sons, Inc., 1991.

The following examples are provided to more fully illustrate the invention, and are not to be construed as limiting the scope of the invention in any manner.

EXAMPLE 1

4-(4-t-Butylphenyl)-2-(4-chlorophenyl)-5-(4-pyridyl)imidazole

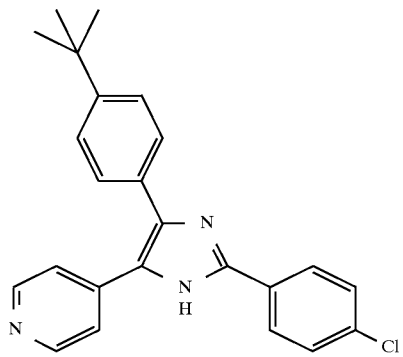

Step A. 4-(t-Butyldimethylsilyloxy)methyl pyridine

At room temperature, 10.9 g of 4-pyridylcarbinol (100 mmol) was treated with 60 mL of DCM followed by 21 mL (150 mmol) of triethylamine. After being cooled to 10° C., 18 g (120 mmol) of t-butyldimethylsilyl chloride (dissolved in 20 mL DCM) was added dropwise. The resulting reaction mixture was warmed to room temperature slowly and stirred overnight. Subsequently, it was filtered over a pad of celite, rinsed with ether. Volatiles were removed and the residue was taken up in hexane and filtered over celite again, washed with hexane/ether, and the solvents removed by rotoevaporation. This was repeated twice. Pumping under high vac of the residue thus obtained provided 22 g (99%) of the desired product as a light brown oil, mass spectrum (CI) m/e=224 (M+1)$^+$.

Step B. 4-Pyridyl-t-butydimethylsilyloxymethyl 4-fluorophenyl ketone

Into a 2 L 3-necked round bottom flask fitted with a thermometer, dry nitrogen gas inlet, addition funnel and mechanical stirrer was added diisopropylamine (65 mL, 0.46 mol) in THF (120 mL). Cooled to −20° C. with a isopropyl alcohol/dry ice bath and added a solution of n-butyllithium in hexanes (210 mL of a 2.5M solution, 0.53 mol). Stirred at −15° C. for 30 min, then cooled to −20° C. Added 4-t-butydimethylsilyloxymethylpyridine from Step A (98.2 g, 0.44 mol) neat over a 30 min period. Let stir for 45 min at −20° C. To this mixture was added a solution of 4-fluoro-N-methoxy-N-methyl-benzamide (84.5 g, 0.46 mol) in THF (90 mL) over a 30 min period. The dark solution was stirred at 0° C. for 1 h, then warmed slowly to room temperature for 30 min. The reaction was poured into water (500 mL) containing ammonium chloride (100 g). After stirring for 10 min at room temperature, the solution was extracted with ethyl acetate (3 times). The combined organic extracts were washed successively with water and saturated salt solution. The combined aqueous layers were extracted with ethyl acetate. The combined ethyl acetate extracts were dried over anhydrous magnesium sulfate. The solution was filtered and the solvent removed by rotoevaporation. The residue was purified by flash column chromatography on silica gel eluted with 15–50% ethyl acetate in hexanes (17 L in total). The solvent was removed by rotoevaporation to yield the tide compound as an amber oil (120.4 g, 74% yield).

Step C: 4-Pyridyl-t-butydimethylsilyloxymethyl 4-t-butylphenyl ketone

To a cooled solution of diisopropylamine (183 mg, 1.81 mmol) in dry THF (0.35 mL) at −20° C. was added a solution of n-butyllithium in hexanes (0.83 mL of a 2.5M solution, 2.08 mmol). Stirred at −20° C. for 1 hr and then added a solution of 4-pyridyl-t-butydimethylsilyloxymethyl 4-fluorophenyl ketone from Step B (383 mg, 1.72 mmol) in THF (0.45 mL). Stirred at −20° C. for 45 min, resulting in a thick yellow-brown solution. A solution of 4-t-butyl-N-methoxy-N-methyl-benzamide (400 mg, 1.81 mmol) in THF (0.5 mL) was added and the solution stirred at −20° to 0° C. for 5 h. The reaction was cooled to −20° C. and quenched by the addition of a saturated ammonium chloride solution. The reaction mixture was then extracted with ethyl acetate (3 times) and the combined extracts washed successively with water (2 times) and saturated salt solution and dried over anhydrous sodium sulfate. The mixture was filtered and the solvent removed by rotoevaporation. The residue was purified by flash column chromatography on silica gel eluted with 5–10% ethyl acetate in hexanes to yield the title compound as a yellow oil (341 mg, 49% yield).

Step D: 4-(4-t-Butylphenyl)-2-(4-chlorophenyl)-5-(4-pyridyl)imidazole

A solution of 4-pyridyl-t-butydimethylsilyloxymethyl 4-t-butylphenyl ketone from Step C (170 mg, 0.44 mmol), copper (II) acetate (161 mg, 0.89 mmol), ammonium acetate (342 mg, 4.44 mmol) and 4-chlorobenzaldehyde (78 mg, 0.56 mmol) in acetic acid (3 mL) was heated to 110° C. for 5 h. The reaction mixture was then cooled to 0° C. and ice (4 g), ethyl acetate (4 mL) and concentrated ammonium hydroxide solution (4 mL) were added. After stirring for 30 min, the phases were separated and the aqueous layer extracted with ethyl acetate (2 times). The combined organic phases were successively washed with water (2 times) and saturated salt solution and dried over anhydrous sodium sulfate. The mixture was filtered and the solvent removed by rotoevaporation. The residue was purified by flash column chromatography on silica gel eluted with 0–3% methanol in methylene chloride to yield the title compound as a pale yellow solid 102 mg, 59% yield), mass spectrum (CI) m/e=388 (M+1)$^+$.

The following compounds were prepared by methods analogous to those described in Example 1 except the appropriately substituted N-methoxy-N-methylbenzamide and substituted benzaldehyde was used in place of 4-t-butyl-N-methoxy-N-methylbenzamide and 4-chlorobenzaldehyde, respectively.

2-(4-chlorophenyl)-4-(3-phenoxyphenyl)-5-(4-pyridyl) imidazole, mass spectrum (CI) m/e=424 (M+1)$^+$.

2-(3-chlorophenyl)-4-(3-phenoxyphenyl)-5-(4-pyridyl) imidazole, mass spectrum (CI) m/e=424 (M+1)$^+$.

2-(3,4-dichlorophenyl)-4-(3-phenoxyphenyl)-5-(4-pyridyl) imidazole, mass spectrum (CI) m/e=458 (M+1)$^+$.

2-(4-phenoxyphenyl)-4-(3-phenoxyphenyl)-5-(4-pyridyl) imidazole, mass spectrum (CI) m/e=482 (M+1)$^+$.

4-(4-n-butylphenyl)-2-(4-chlorophenyl)-5-(4-pyridyl) imidazole, mass spectrum (CI) m/e=388 (M+1)$^+$.

4-(4-n-butylphenyl)-2-(3-chlorophenyl)-5-(4-pyridyl) imidazole, mass spectrum (CI) m/e=388 (M+1)$^+$.

4-(4-t-butylphenyl)-2-(3-chlorophenyl)-5-(4-pyridyl) imidazole, mass spectrum (CI) m/e=388 (M+1)$^+$.

2-(4-chlorophenyl)-4-(4-n-propyloxyphenyl)-5-(4-pyridyl) imidazole, mass spectrum (CI) m/e=390 (M+1)$^+$.

2-(4-chlorophenyl)-4-(4-ethylthiophenyl)-5-(4-pyridyl) imidazole, mass spectrum (CI) m/e=392 (M+1)$^+$.

4-(3-phenoxyphenyl)-5-(4-pyridyl)-2-(4-trifluoromethylphenyl)-imidazole, mass spectrum (CI) m/e=458 (M+1)$^+$.

2-(4-bromophenyl)-4-(3-phenoxyphenyl)-5-(4-pyridyl) imidazole, mass spectrum (CI) m/e=468, 470 (M+1)$^+$.

2-(4-fluorophenyl)-4-(3-phenoxyphenyl)-5-(4-pyridyl) imidazole, mass spectrum (CI) m/e=408 (M+1)$^+$.

2-(4-benzyloxyphenyl)-4-(3-phenoxyphenyl)-5-(4-pyridyl) imidazole, mass spectrum (CI) m/e=496 (M+1)$^+$.

2-(3-fluorophenyl)-4-(3-phenoxyphenyl)-5-(4-pyridyl) imidazole, mass spectrum (CI) m/e=408 (M+1)$^+$.

4-(3-n-butyloxyphenyl)-2-(4-chlorophenyl)-5-(4-pyridyl) imidazole, mass spectrum (CI) m/e=404 (M+1)$^+$.

4-(2-n-butyloxyphenyl)-2-(4-chlorophenyl)-5-(4-pyridyl) imidazole, mass spectrum (CI) m/e=404 (M+1)$^+$.

4-(4-benzyloxyphenyl)-2-(4-chlorophenyl)-5-(4-pyridyl) imidazole, mass spectrum (CI) m/e=438 (M+1)$^+$.

EXAMPLE 2

2-(4-chlorophenyl)-4-(2,4-di(n-propyloxy)phenyl)-5-(4-pyridyl)imidazole

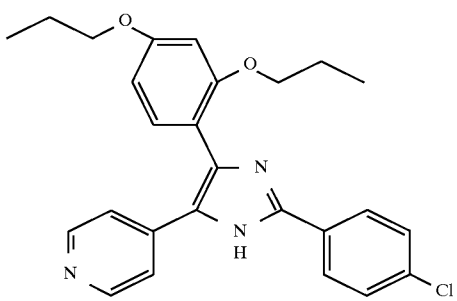

Step A: 2,4-dihydroxy-N-methoxy-N-methyl-benzamide

To a cooled solution of 2,4-dihydroxybenzoic acid (8 g, 52 mmol), N,O-dimethylhydroxylamine hydrochloride (6.1 g, 62 mmol) and N-methylmorpholine (13.18 g, 130 mmol) in methylene chloride (50 mL) at 0° C. was added EDC batchwise (11.95 g, 62.3 mmol). Stirred at room temperature for 3 days. The reaction was quenched by the addition of water and then extracted with methylene chloride (2 times). The combined organic extracts were successively washed with a 10% aqueous citric acid solution, a 5% sodium bicarbonate solution, water and saturated salt solution and dried over anhydrous sodium sulfate. The mixture was filtered and the solvent removed by rotoevaporation. The residue was purified by flash column chromatography on silica gel eluted with 0–33% ethyl acetate in hexanes to yield the title compound, mass spectrum (CI) m/e=198 (M+1)$^+$.

Step B: 2,4-Di-n-propyloxy-N-methoxy-N-methyl-benzamide

To a solution of 2,4-dihydroxy-N-methoxy-N-methyl-benzamide (250 mg, 1.27 mmol) in DMF (1 mL) was added solid potassium carbonate (351 mg, 2.54 mmol) and 1-bromopropane (343 mg, 2.79 mmol). The reaction mixture was stirred overnight at 55° C. The reaction was quenched by the addition of an aqueous solution of 10% citric acid. The mixture was extracted with ethyl acetate (2 times). The combined organic extracts were successively washed with water and saturated salt solution and dried over anhydrous sodium sulfate. The mixture was filtered and the solvent removed by rotoevaporation. The residue was purified by flash column chromatography on silica gel eluted with 0–50% ethyl acetate in hexanes to give the title compound, mass spectrum (CI) m/e=282 (M+1)$^+$.

Step C: 2,4-Di-n-propyloxyphenyl 4-pyridylmethyl ketone

To a cooled solution of lithium diisopropylamide (generated from diisopropylamine (109 mg, 1.07 mmol) and a solution of n-butyllithium in hexanes (0.49 mL of a 2.5M solution, 1.22 mmol)) in THF (0.5 mL) at −78° C. was added 4-picoline (95 μL, 0.98 mmol). Stirred −78° to 0° C. for 1 h. The reaction mixture was cooled to −78° C. and a solution of 2,4-di-n-propyloxy-N-methoxy-N-methyl-benzamide from Step B (274 mg, 0.98 mmol) in THF (0.5 mL) was added dropwise. The reaction was stirred <0° C. for 4 h and then quenched by the addition of a saturated aqueous solution of ammonium chloride. The mixture was extracted with ethyl acetate (2 times). The combined extracts were successively washed with water and saturated salt solution and dried over anhydrous sodium sulfate. The solution was filtered and the solvents removed by rotoevaporation. The residue was purified by flash column chromatography on silica gel eluted with 0–50% ethyl acetate in hexanes to yield the title compound (147 mg, 48% yield), mass spectrum (CI) m/e=314 (M+1)$^+$.

Step D: 1-(24-Di-n-propyloxyphenyl)-2-(4-pyridyl) ethane-1,2-dione

To an oxygen-free solution of 2,4-di-n-propyloxyphenyl 4-pyridylmethyl ketone (142 mg, 0.45 mmol) in acetic acid (3.4 mL) was added selenium dioxide (50.3 mg, 0.45 mmol). The reaction was stirred at 90° C. for 1 h, then cooled to 0° C. The reaction was quenched by the addition of a solution of potassium carbonate until the pH=8. The mixture was then extracted with ethyl acetate ( 2 times) and the combined extracts successively washed with water and saturated salt solution and dried over anhydrous sodium sulfate. The solution was filtered and the solvent removed by rotoevaporation. The residue was purified by flash column chromatography on silica gel eluted with 50% ethyl acetate in hexanes to yield the title compound as a sticky yellow gum (65 mg, 44% yield), mass spectrum (CI) m/e=328 (M+1)$^+$.

Step E: 2-(4-Chlorophenyl)-4-(2,4-di(n-propyloxy) phenyl)-5-(4-pyridyl)imidazole A solution of 1-(2,4-di-n-propyloxyphenyl)-2-(4-pyridyl) ethane-1,2-dione from Step D (61 mg, 0.19 mmol), ammonium acetate (144 mg, 1.87 mmol) and 4-chlorobenzaldehyde (33 mg, 0.23 mmol) in acetic acid (1.5 mL) was heated to 100° C. for 3.5 h. After cooling to 0° C., the ice (4g), ethyl acetate (2 mL) and a concentrated solution of ammonium hydroxide was added until the pH was 10. The layers were separated and the aqueous layer extracted with ethyl acetate. The combined organic extracts were successively washed with water and saturated salt solution and dried over anhydrous sodium sulfate. The mixture was filtered and the solvent removed by rotoevaporation. The residue was purified by flash column chromatography on silica gel eluted with 0–3% methanol in methylene chloride to yield the title compound as a cream-colored solid (25 mg, 30% yield), mass spectrum (CI) m/e=448 (M+1)$^+$.

The following compound was prepared by methods analogous to those described in Example 1 except in Step B, 1-bromobutane was substituted for 1-bromopropane:

2-(4-chlorophenyl)-4-(2,4-di(n-butyloxy)phenyl)-5-(4-pyridyl)imidazole, mass spectrum (CI) m/e=476 (M+1)$^+$.

BIOLOGICAL ASSAYS

The ability of compounds of the present invention to inhibit the binding of glucagon and the synthesis or the activity of cytokines can be determined by the following in vitro assays.

$^{125}$I-Glucagon Binding Screen with CHO/hGLUR Cells

The reagents are prepared as follows:

1M o-Phenanthroline (Aldrich #32,005–6,MW 198.23) (prepare fresh): 198.2 mg/ml ethanol 0.5M DTT (Sigma #D-9779,MW 154.2) (prepare fresh).

Protease Inhibitor Mix(1000X): 5 mg leupeptin +10 mg benzamidine +40 mg bacitracin +5 mg soybean trypsin inhibitor per ml DMSO. Store aliquots at −20° C.

250 µM Human Glucagon (Peninsula #7165,MW 3480.62): Solubilize 0.5 mg vial in 575 µl 0.1N acetic acid. Store in aliquots at −20° C. Thus, 1 µl yields 1 µM final concentration in assay for non-specific binding.

Assay Buffer: 20 mM Tris, pH 7.8; 1 mM DTT; 3 mM o-phenanthroline.

Assay Buffer w/ 0.1% BSA (for dilution of label only, therefore 0.01% final in assay): 10 µl 10% BSA (heat-inactivated) +990 µl assay buffer $^{125}$I-Glucagon (NEN #NEX-207, receptor-grade, 2200 Ci/mmol):

Dilute to 50,000 cpm/25 µl in assay buffer w/ BSA. Thus, ~50 pM final concentration in assay.

Harvesting of CHO/hGLUR Cells for Assay:

1. Remove media from confluent flask then rinse once each with PBS (Ca,Mg-free) and Enzyme-free Dissociation Fluid (Specialty Media, Inc.).

2. Add 10 ml Enzyme-free Dissoc. Fluid and hold for ~4 min. at 37° C.

3. Gently tap cells free, triturate, take aliquot for counting and centrifuge remainder for 5 min. at 1000 rpm.

4. Resuspend pellet in assay buffer (no BSA) at 75000 cells per 100 µl.

Alternatively, membrane preparations from CHO/hGLUR cells can be used in place of whole cells at the same assay volume. Final protein concentration of membrane preparation is determined on a per batch basis.

The determination of inhibition of glucagon binding is carried out by measuring the reduction of $^{125}$I-glucagon binding in the presence of compounds of Formula I. The assay is carried out in a 96-well box. The following reagents are combined:

|  | Assay Buffer | Compound/ Vehicle | 250 µM Glucagon | $^{125}$I-Glucagon | CHO/ hGLUR Cells |
|---|---|---|---|---|---|
| Total Binding | 120 µL | —/5 µL | — | 25 µL | 100 µL |
| +compound | 120 µL | 5 µL/— | — | 25 µL | 100 µL |
| NSB | 120 µL | —/5 µL | 1 µL | 25 µL | 100 µL |

NSB: non specific binding

The box is incubated for 60 min. at 22° C. on a shaker at 275 rpm. The wells are filtered over pre-soaked (0.5% polyethylimine(PEI)) GFIC filtermat using an Innotech Harvester or Tomtec Harvester with four washes of ice-cold 20 mM Tris, pH 7.8 buffer. Count filters in Gamma-scintillation counter.

What is claimed is:

1. A compound of formula (I):

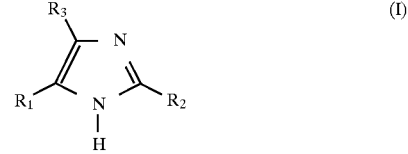

wherein $R_1$ is 4-pyridyl;

$R_2$ is phenyl, 1-naphthyl or 2-naphthyl each of which is unsubstituted or substituted with one or two substituents each of which is independently selected from the group consisting of (1) $C_{1-10}$ alkyl, (2) $R_4$, and (3) $C_{1-10}$ alkyl substituted with up to 5 groups independently selected from halogen $R_3$ is phenyl substituted with one or two substituents each of which is independently selected from the group consisting of meta-O-phenyl, which is optionally substituted with halo; $C_{1-4}$ alkyl, or $C_{1-4}$ alkoxy;

$R_4$ is (1) —$OR_8$, (2) halogen;

$R_8$ is $R_{11}$;

$R_{11}$ is (1) $C_{1-10}$ alkyl, (2) halo-substituted $C_{1-10}$ alkyl, (3) $C_{3-7}$ cycloalkyl, (4) aryl, (5) aryl-$C_{1-10}$ alkyl, or a pharmaceutically acceptable salt thereof.

2. A compound of claim 1 selected from the group consisting of:

(1) 2-(4-chlorophenyl)-4-(3-phenoxyphenyl)-5-(4-pyridyl)imidazole,
(2) 2-(3-chlorophenyl)-4-(3-phenoxyphenyl)-5-(4-pyridyl)imidazole,
(3) 2-(3,4-dichlorophenyl)-4-(3-phenoxyphenyl)-5-(4-pyridyl)imidazole,
(4) 2-(4-phenoxyphenyl)-4-(3-phenoxyphenyl)-5-(4-pyridyl)imidazole,
(5) 4-(3-phenoxyphenyl)-5-(4-pyridyl)-2-(4-trifluoromethylphenyl)-imidazole,
(6) 2-(4-bromophenyl)-4-(3-phenoxyphenyl)-5-(4-pyridyl)imidazole,
(7) 2-(4-fluorophenyl)-4-(3-phenoxyphenyl)-5-(4-pyridyl)imidazole,
(8) 2-(4-benzyloxyphenyl)-4-(3-phenoxyphenyl)-5-(4-pyridyl)imidazole.

3. A pharmaceutical composition comprising a compound according to claim 1 and a pharmaceutically acceptable carrier.

* * * * *